United States Patent [19]

Timm et al.

[11] Patent Number: 4,541,420
[45] Date of Patent: Sep. 17, 1985

[54] PENILE PROSTHESIS UTILIZING PATIENT CONTROLLED CAM ACTUATOR APPARATUS

[75] Inventors: Gerald W. Timm, San Juan Capistrano, Calif.; Richard A. Helms, Elk River; Donald L. Sandford, Lauderdale, both of Minn.

[73] Assignee: Dacomed Corporation, Minneapolis, Minn.

[21] Appl. No.: 604,022

[22] Filed: Apr. 26, 1984

[51] Int. Cl.⁴ .............................................. A61F 5/00
[52] U.S. Cl. ...................................... 128/79; 623/11; 623/12
[58] Field of Search ............... 128/79; 3/1; 52/108

[56] References Cited

U.S. PATENT DOCUMENTS

| | | | |
|---|---|---|---|
| 3,349,526 | 10/1967 | Schuster | 52/108 |
| 3,411,376 | 11/1968 | Weber et al. | |
| 3,436,983 | 4/1969 | Krantz | |
| 3,492,768 | 2/1970 | Schuster | 52/113 |
| 3,954,102 | 5/1976 | Buuck | 128/79 |
| 3,987,789 | 10/1976 | Timm et al. | 128/79 |
| 4,066,073 | 1/1978 | Finney et al. | 128/79 |
| 4,151,840 | 5/1979 | Barrington | 128/79 |
| 4,151,841 | 5/1979 | Barrington | 128/79 |
| 4,187,839 | 2/1980 | Nuwayser et al. | 128/79 |
| 4,392,562 | 7/1983 | Burton et al. | 128/79 |

*Primary Examiner*—Stephen C. Pellegrino
*Attorney, Agent, or Firm*—Merchant, Gould, Smith, Edell, Welter & Schmidt

[57] ABSTRACT

A bistable penile prosthesis (20) designed to be surgically implanted in the penis for the treatment of erectile impotence. The prosthesis includes an articulated column (26) and an actuator apparatus (30) enclosed within an outer elongated sheath (28). The actuator apparatus (30) is configured and disposed for alternately compressing the articulated column (26) and tensioning a tension member (32) whereby frictional resistance increases causing an erect state, and stretching the articulated column (26) and relaxing the tension member (32) whereby frictional resistance decreases causing a flaccid state under volitional control by the patient. The actuator (30) includes a cam member (68) defining a pathway for travel therealong by a cam follower member (86) in only one direction.

7 Claims, 8 Drawing Figures

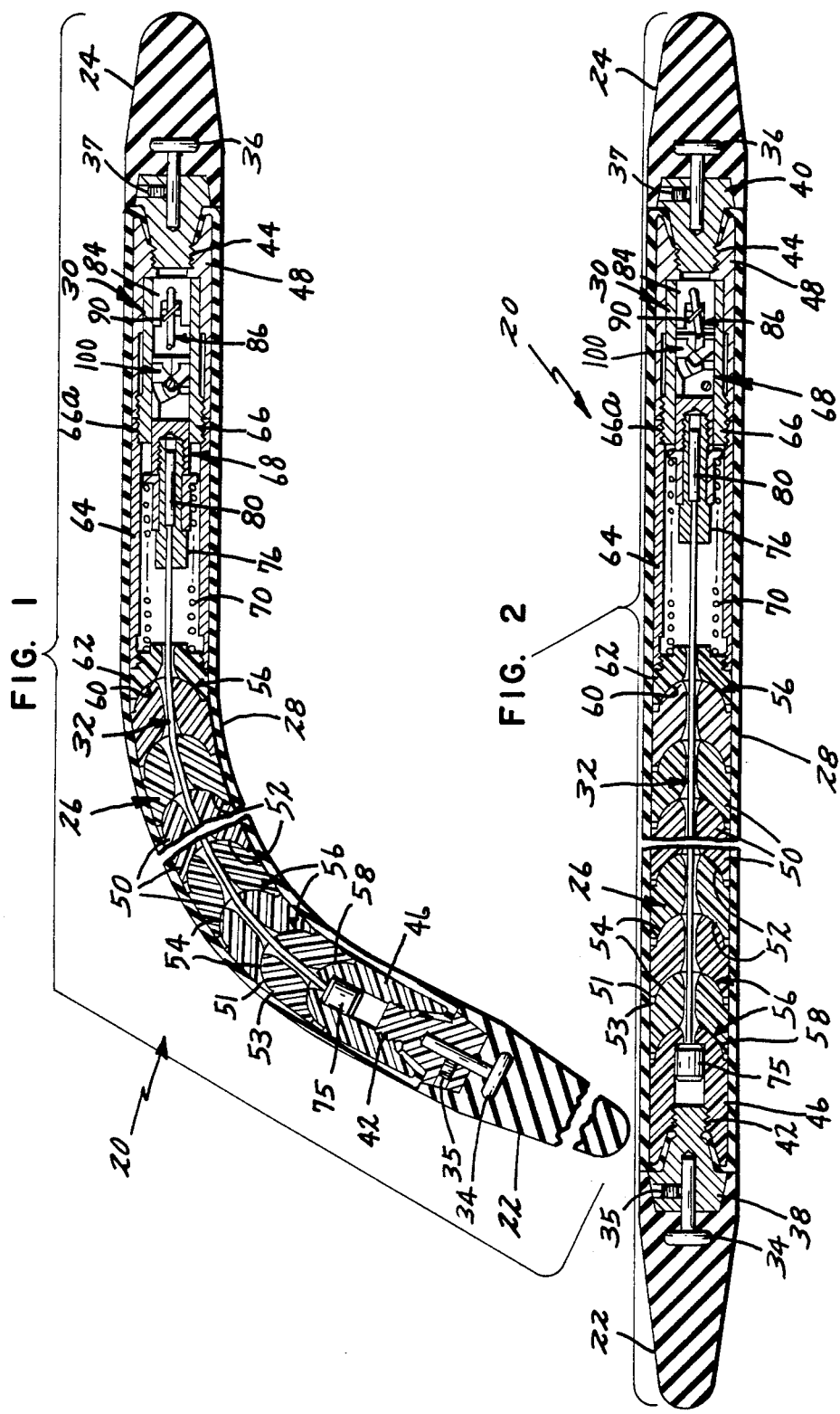

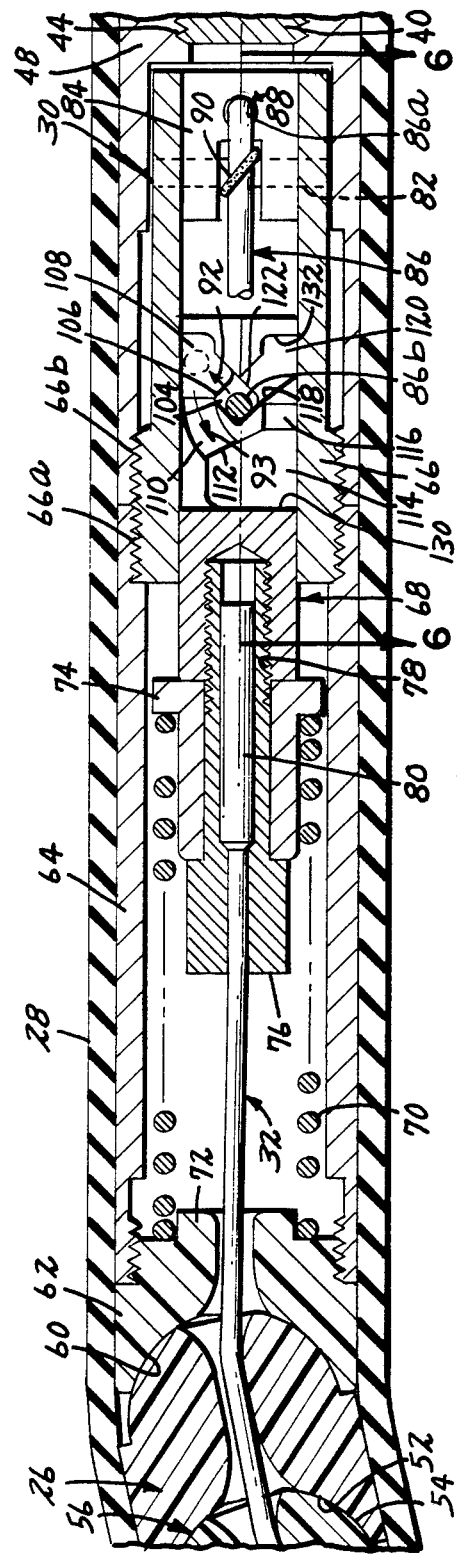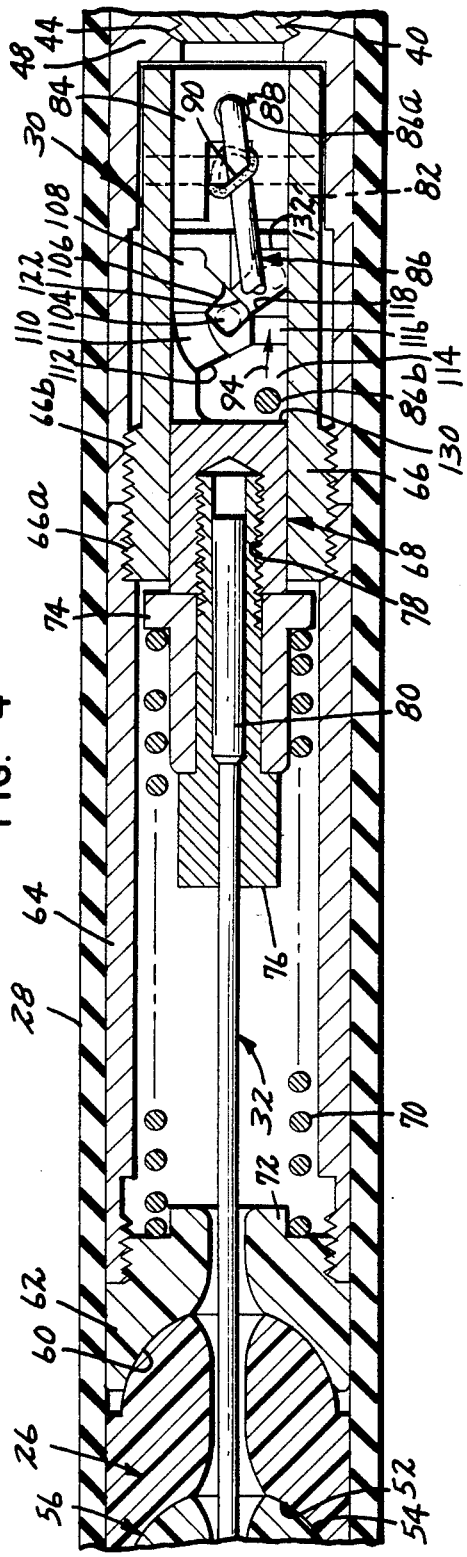

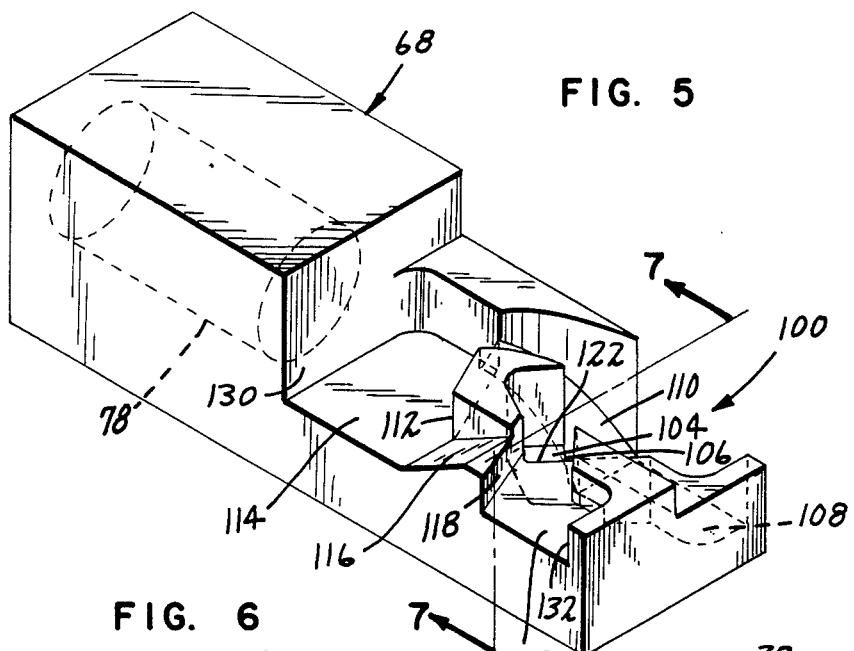
FIG. 5
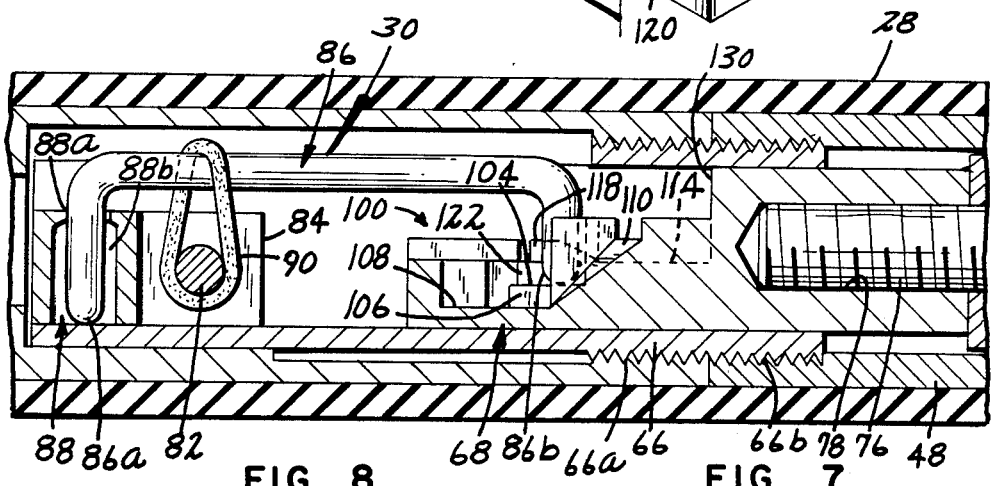
FIG. 6
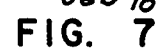
FIG. 8   FIG. 7
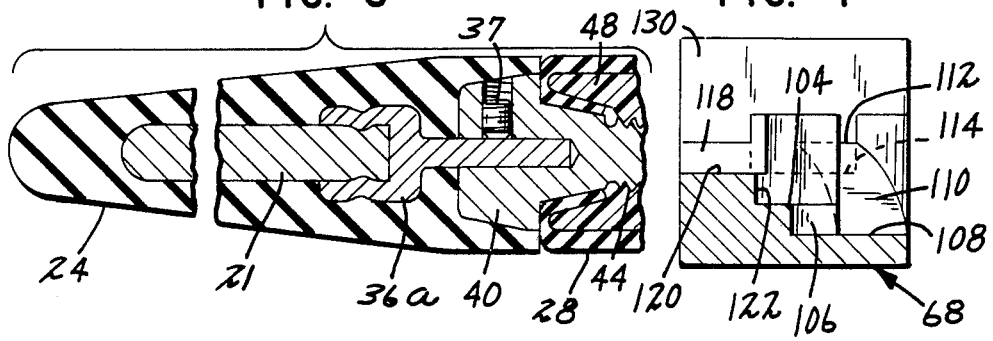

PENILE PROSTHESIS UTILIZING PATIENT CONTROLLED CAM ACTUATOR APPARATUS

BACKGROUND OF THE INVENTION

This invention relates to a penile prosthesis. More particularly, the present invention relates to a penile prosthesis which includes a patient controlled cam actuator providing for volitional control of penile erection and return thereof to a flaccid condition.

The causes of male impotence are many and varied. Various approaches to treating impotence have been developed over the past two decades. Penile prostheses have been implanted within the penis to simulate an erectile state. For example, in Timm et al, U.S. Pat. No. 3,987,789, there is disclosed a prosthesis including an elongated malleable rod portion housed within a generally tubular physiologically inert plastic body. The malleable rod portion enables the prosthesis to be conformed to a variety of shapes by bending or twisting. During intercourse the prosthesis will maintain the penis in an erectile state and afterwards the penis may be positioned and maintained by the user in a convenient, comfortable position. The prosthesis depends upon its malleability to permit moving the penis to a convenient confortable position. The flexibility and similar characteristics of the prosthesis are not controllable by the patient.

U.S. Pat. No. 3,954,102 to Buuck shows a penile erection system having two conditions. In one condition, the implanted prosthesis is controlled by varying the amount of fluid in cylinders within the prosthesis by squeezing an elastomeric bulb through the patient's skin to transfer fluid from a reservoir into cylinders in the prosthesis. Because the reservoir and bulb are positioned outside of the prothesis within the patient's body, the implantation procedure is quite complex and the extensive tubing required to interconnect the various portions of the system increase the possibility of failure of the system.

Other implantable prosthesis have been developed which incorporate a reservoir pump and valving into the prosthesis itself as shown for example, in U.S. Pat. Nos. 4,369,771 and 4,353,360. Those systems still require pump and valving apparatus to be installed within the prosthesis and require the transfer of fluid from a reservoir into an inflatable portion for operation.

The present invention solves these and many other problems associated with currently available devices.

SUMMARY OF THE INVENTION

The present invention relates to a bistable penile prosthesis having an erect state and a flaccid state. The prosthesis includes an elongated cylindrical body having a longitudinal axis and a distal end portion and a proximal end portion. The elongated cylindrical body is bendable between a first curved configuration and a second configuration, the elongated cylindrical body having less curvature in the second configuration than in the first curved configuration. An articulated column of radiused segments is disposed intermediate of the distal end portion and the proximal end portion. Adjacent ones of the segments cooperate to form slideable joints between the adjacent ones of the segments. An outer elongated sheath formed from physiologically inert and pliable material encloses the articulated column. Actuator means is disposed intermediate of the articulated column and one of the distal and proximal end portions. The actuator means includes cam means and cam follower means, the cam means providing a pathway for only one way travel therealong by said cam follower means, Biasing means cooperates with the actuator means to longitudinally bias the cam means and the cam follower means toward one another. Tension means cooperate with the actuator means to longitudinally bias the cam means and the cam follower means away from one another when the tension means is placed in tension. The tension means causes the cam means and the cam follower means to move longitudinally away from one another when the elongated cylindrical body of the prosthesis is bent into the first configuration. The biasing means longitudinally moves the cam means and the cam follower means toward one another when the elongated cylindrical body of the prosthesis is returned to the second configuration. The cam means and the cam follower means come to rest at a first or second relative longitudinal displacement between one another upon return of the elongated cylindrical body of the prosthesis to the second configuration. The cam means and the cam follower means are farther apart when positioned in the first relative longitudinal displacement. The prosthesis is in the erect state when the cam means and the cam follower means are in the second relative longitudinal displacement and in the flaccid state when the cam means and the cam follower means are in the first relative longitudinal displacement.

The invention provides for a mechanical patient-controlled device for inducing penile erection upon manual activation. In particular, the invention is a surgically implantable mechanical penile prosthesis composed of an elongated cylindrical device which employs an articulated column characterized by a series of segments with slidable alternating ball and socket joints therebetween. The normal flexibility of the device permits the penis to normally remain in a flaccid state.

The prosthesis of the present invention is particularly advantageous in that it can be implanted surgically within the penis without regard to angular orientation thereby avoiding the possibility of failure if during implant or in use, the prosthesis partially rotates about its longitudinal axis. Accordingly, the prosthesis is designed to be generally symmetrical about its longitudinal axis.

Furthermore, the present invention provides for volitional control of erection, generating sufficient stiffness of the penis for intercourse, and permits user deactivation, whereby the penis recovers as a flaccid state.

Yet another advantageous feature of the present invention is that it readily enables patient activation and deactivation.

Furthermore, the present invention is designed to be implanted by conventional surgical procedures and is biologically compatible with the human body environment.

In addition, the present invention provides for activation/deactivation over many cycles of use.

Furthermore, the present invention enables the penis to obtain a flaccid state when the prosthesis is deactivated and provides sufficient rigidity for intercourse when the prosthesis is activated.

The present invention provides for greater rigidity when in the erect state and greater flaccidity and comfortable concealment when in the flacid state. In the flaccid state the prosthesis will hang downwardly due to the weight of the prosthesis and the penis so as to have a somewhat natural configuration.

Furthermore, the present invention is suitable for long term implants.

Additionally the present invention provides a prosthesis which can withstand higher loads while utilizing an actuator apparatus which functions in a small and confined space.

The present invention provides a prosthesis which includes a totally self-contained actuator apparatus for mechanically controlling the two phases of penile erection, the erect phase and the flaccid phase.

A preferred embodiment of the present invention is bistable. In other words it operates in either a flexible or a stiffened mode at the user's control. Activation and deactivation is achieved by manual bending of the penis, whereupon the prosthesis is alternately rigid or flaccid. Bending of the prosthesis places a tension member in tension which causes a a cam member of the actuator aparatus to be axially displaced, the actuator apparatus alternately securing the prosthesis in a deactivated, flaccid state or an activated, erect state.

In the preferred embodiment of the present invention, the articulated column is axially journaled about the longitudinally extending tension member. When the prosthesis is activated, the increased tension in the tension member and the compression of the articulated column induces a stress state in the prosthesis that displays bending stiffness. This is attributable to: (1) interfacial friction between the spheres and sockets in the column and (2) tension in the tension member.

Also in the preferred embodiment of the present invention, the actuator apparatus includes a cam member having a generally heart shaped ramp configuration and a cam follower member adapted for following said ramp configuration in only one direction. The cam member is slidably mounted for axially movement of the prosthesis and is interconnected to the tension member and is further biased away from the articulated column by a biasing member. Alternate bending of the prosthesis places the tension member in tension and causes the cam member to be displaced axially whereupon the cam follower follows the ramp configuration of the cam member. Upon ceasing the bending process, the cam member returns to a first longitudinal position or a second longitudinal position such that the prosthesis is in a flaccid state or an erect state.

Yet another feature of the preferred embodiment is that the articulated column includes a plurality of bend limiting segments forming cooperating ball and socket joints therebetween. The bend limiting segments have cooperating shoulder portions which limit the amount of pivotal movement of adjacent bend limiting segments.

Yet another feature of the preferred embodiment is the provision for varying sizes of distal and proximal end portions which are removably interconnected to the prosthesis to modify the overall length of the prosthesis to accommodate normal variations in the patient's intracorporal cavenosal length.

Still another feature of the preferred embodiment is the inclusion of a stiffening member providing additional rigidity to the distal end portion.

These and various other advantages and features of novelty which characterize the invention are pointed out with particularity in the claims annexed hereto and forming a part hereof. However, for a better understanding of the invention, its advantages, and objects attained by its use, reference should be had to drawings which form a further part hereof, and to the accompanying descriptive matter, in which there is illustrated and described a preferred embodiment of the invention.

BRIEF DESCRIPTION OF THE DRAWINGS

In the drawings, in which like reference numerals and letters indicate corresponding parts throughout the several views:

FIG. 1 is a longitudinal axial sectional view of a preferred embodiment of the present invention in a deactivated or flaccid state;

FIG. 2 is a longitudinal axial sectional view of the embodiment shown in FIG. 1 in an activated or erect state;

FIG. 3 is an enlarged axial sectional view with portions broken away of the actuator apparatus of the embodiment shown in FIG. 1 in the deactivated or flaccid state;

FIG. 4 is an enlarged axial sectional view with portions broken away of the actuator apparatus of the embodiment shown in FIG. 2 in the activated or erect state;

FIG. 5 is an enlarged elevational view of the cam member of the actuator apparatus shown in FIGS. 1 and 2;

FIG. 6 is a sectional view as generally seen along line 6—6 of FIG. 3;

FIG. 7 is a sectional view as generally seen along line 7—7 in FIG. 5; and

FIG. 8 is an enlarged sectional view of an alternate embodiment of the distal end portion.

DETAILED DESCRIPTION OF A PREFERRED EMBODIMENT OF THE PRESENT INVENTION

Referring now to the drawings, a preferred embodiment of a mechanical penile prosthesis in accordance with the principles of the present invention is illustrated in FIGS. 1 and 2, the penile prosthesis generally being referred to by the reference numeral 20. The prosthesis 20 is generally shown as an elongated member including a proximal end portion 22 and a distal end portion 24. An elongated articulated column 26 is positioned between the proximal and distal end portions 22 and 24 enabling pivotal or bending motion of the prosthesis 20 in all directions (360 degrees) about the longitudinal axis of the prosthesis 20. Interposed between the distal end of the articulated column 26 and the distal end portion 24 is an actuator apparatus 30. It will be appreciated that in other embodiments, the acutator apparatus 30 might be located between the proximal end portion 22 and the articulated column 26. The articulated column 26 is axially journaled about an axially extending elongated tension member 32 which extends from proximate the proximal end of the articulated column 26 to proximate the proximal end 22 of the actuator apparatus 30. The articulated column 26 and the actuator apparatus 30 are enclosed by a sheath 28 of physiologically inert and pliable material, preferably polytetrafluoroethylene which shields the prosthesis 20 from body tissue so as to prevent the growth of body tissue into the inner working elements of the prosthesis which would otherwise affect operation of the working elements of the prosthesis and interfere with its proper function. In addition, such growth of body tissue into the prosthesis might also result in damage to the body tissue. Accordingly, the sheath 28 also prevents tissue damage.

The actuator apparatus 30 in cooperation with the tension member 32 and the articulated column 26 provides the preferred embodiment of the present invention with bistable characteristics, i.e. the prosthesis 20 may be manually activated to a rigid/erect state as generally illustrated in FIG. 2 or deactivated to a flexible/flaccid state as generally indicated in FIG. 1. The prosthesis 20 remains in either of these two states until manually activated or deactivated.

The prosthesis 20 of the present invention is designed for implantation in the intracorporal cavernosal of the penis by conventional surgical procedures for treatment of erectile impotence. The prosthesis 20 is configured to generally match penile intracorporal cavernosal size so as to extend sufficiently proximally and distally when anchored within the penis and body cavity so as to induce an erected penile state generating sufficient stiffness of the penis for intercourse when activated and to provide the penis with flaccid characteristics when deactivated.

Accordingly, the present invention provides for volitional control of penile erection and return thereof to a flaccid state. Furthermore, the configuration of the present invention enables surgical implantation without regard for angular orientation and prevents malfunction if angular rotation is realized during use. In addition, the present invention is biologically compatible with the human body environment and enables activation/deactivation over many repetitive cycles of use.

More particularly, the proximal end portion 22 is tapered to assist in anchoring the prosthesis 20 in the body and the distal end portion 24 is bullet-or cone-shaped to adapt to the distal end of the penis. The proximal end portion 22 and the distal end portion 24 are provided in various lengths to accommodate normal variations in the patient's intracorporal cavernosal length, preferably ranging from one to eight centimeters. The appropriate length for each is selected at the time of implant as determined by the incision site and by the patient's total intracorporal cavernosal length. Preferably, the proximal end portion 22 and the distal end portion 24 are made from a semi-rigid material such as silicone rubber.

The proximal end portion 22 and the distal end portion 24 are attached to the segmented, flexible body of the prosthesis 20. This might be accomplished in any of several ways such as by a positive locking, snap-on mechanism (not shown) or by threaded attachment of the end portions 22, 24 to the flexible body of the prosthesis 20. In the preferred embodiment, as generally illustrated in FIGS. 1 and 2, elongated T-shaped stainless steel pin members 34, 36 are securedly molded or embedded in the proximal end portion 22 and the distal end portion 24, respectively. The T-shaped pin members 34, 36 are slideably inserted into cylindrical apertures located in claim members 38, 40 respectively. The T-shaped pin members 34, 36 are retained in the aperatures of the clamp members 38, 40 by Titanium set screws 35 and 37. It will be appreciated that in the embodiment shown, the end portions 22, 24 may be readily replaced during the implantation process, if necessary, by simply folding back the sili cone rubber material enclosing the set screws 35, 37 so that a hex-wrench can be utilized to loosen the set screws 35, 37. The clamps members 38, 40 in turn are threadedly attached at 42, 44, respectively to the flexible body of the prosthesis. The clamp members 38, 40 cooperate with wedge shaped members 46, 48, which are configured to receive the clamp members 38, 40 such that the end portions of the sheath 28 are wedged between the clamp members 38, 40, and the inside sloping walls of the members 46, 48. Accordingly, the sheath 28 is retained in position at the proximal and the distal end portions of the prosthesis 20.

As illustrated in FIG. 8, in an alternate embodiment of the distal end portion 24, particularly in the longer versions, a polymeric reinforcing rod 21 might be molded therein to provide extra stiffness. The reinforcing rod 21 is wedged and crimped into a modified pin member 36a designed for the longer distal end portion 24. The reinforcing rod 21 provides sufficient rigidity to prevent buckling but provides suffficent resiliency to provide for some bending action such that the reinforcing rod 21 can be concealed within the silicone rubber of the end portion 24 and yet not break or erode through the surfaces thereof after extended used thereof.

The articulated column 26 comprises a plurality of radiused segments 50. Each of the segments 50 has a concave surface 52 and a convex surface 54, the segments 50 being oriented such that the adjacent surfaces of the segments 50 cooperate to form ball and socket joints 56. The articulated column 26 is journaled axially to receive the tension member 32. The segments 50 as well as the other internal parts of the prosthesis are made from a surgically implantable material, preferably an implantable plastic, such as polyurethane, polysulfone, or polypropolene.

It will be appreciated that in alternate embodiments of the present invention, other elements with slidable cooperating surfaces may be utilized to form an articulated column.

In the preferred embodiment as illustrated in FIGS. 1 through 4, the segments 50 include a shoulder portion 51 about the periphery of the concave surface 52 and a corresponding shoulder portion 53 about the periphery of the convex surface 54, the shoulder portions 51, 53 of adjacent segments 50 cooperate to limit the amount of bending or pivotal movement which can occur at the junction of any two adjacent segments 50.

In the embodiment illustrated, the member 46 to which the sheath 28 is clamped, has a generally convex surface 58 adjacent the proximal end of the articulated column 26 to form a ball and socket joint with the articulated column 26.

Furthermore, a segment 62 at the distal end of the articulated column 26 and interconnected to the member 48 has a concave surface 60 thereby forming a ball and socket joint with the articulated column 26.

As shown in FIGS. 1 and 2, disposed intermediate of the distal end portion 24 and the distal end portion of the articulated column 26 is the actuator apparatus 30. It will be appreciated, that the actuator apparatus 30 might also be disposed intermediate of the proximal end portion 22 and the articulated column 26; however, for purposes of this specification the actuator apparatus 30 will be presumed to be positioned proximate the distal end portion 24.

The radiused segment 62 is threadedly interconnected at a distal end to a hollow housing 64 which is coaxially positioned within the sheath 28. The hollow housing 64 is in turn threadedly interconnected at an opposite end to a threaded position 66a of a guide member 66 which is coaxially positioned within the sheath 28 and serves as a longitudinal guide for a cam member 68 illustrated in more detail in FIG. 5. As illustrated in FIG. 5, the cam member 68 has a generally rectangular base configuration. Accordingly, the guide member 66 defines a rectangular U-shaped channel which is open on a side facing the top of the cam member 68. The guide member 66 is in turn fixed against longitudinal movement by being threadedly attached to the segment 48 along a threaded portion 66b.

As illustrated in FIGS. 3 and 4, the housing 64 serves as a spring casing for a coil spring 70 which is mounted between a spring seat 72 on the segment 62 and a spring seat 74 adjacent the proximal end of the cam member 68. The coil spring is coaxially positioned about the tension member 32 which is fixedly secured at its proximal end by an anchor member 75 pivotally mounted in the member 46 and fixedly secured at its distal end by an anchor member 76 threadedly attached to a threaded aperture 78 in the cam member 68. The anchor member 76 cooperates with a member 80 crimped onto the end of the tension member 32 to securely anchor the tension member 32 to the cam member 68.

As illustrated in FIGS. 3 and 4, fixed against longitudinal movement by a cross pin 82 interconnected to the guide member 66 is a stationary mounting block 84 which pivotally supports a cam follower member 86 at a first end 86a in an aperture 88 for pivotal motion about an axis transverse with respect to the longitudinal axis of the prosthesis 20. As illustrated in FIG. 6, the aperture 88 has a narrowed portion 88a roughly the diameter of the end 86a and an enlarged portion 88b. The aperture 88 extends completely through the mounting block 84. The cam follower member 86 is retained in the aperture 88 by an O-ring 90, which might be made of silicone rubber, positioned around the cross pin 82 and the cam follower member 86 intermediate of the first end 86a and a second end 86b of the cam follower member 86.

As further illustrated in FIGS. 5 through 7, the cam member 68 has a generally heart shaped ramp configuration 100 with a plurality of horizontal surfaces, ramps, and vertically extending barriers providing for only one way travel therealong as generally indicated by the arrows 92, 93 and 94 in FIGS. 3 and 4 by the end 86b of the cam follower member 86 as the cam member 68 moves longitudinally of the prosthesis 20. The O-ring 90 also serves to bias the cam follower member 86 downwardly onto the ramp configuration 100 and the guide member 66 facilitates in retention of the cam follower end 86b on the ramp configuration 100.

In operation, the prosthesis 20 is activated by manually bending the prosthesis 20 downwardly into a curved shape. The bending action causes a displacement of the tension member 32, which because of its fixed length, results in increased tension in the tension member 32. When the force in the tension member 32 exceeds that of the coil spring 70, the cam member 68 moves longitudinally toward the articulated column 26. The geometry of the ramp configuration 100 is such that movement of the cam member 68 causes the cam follower 86 to move through the one way pattern on the ramp configuration 100. This movement causes the cam follower 86 to alternately lock the prosthesis 20 in the flaccid/flexible state as illustrated in FIGS. 1 and 3 and the erect/rigid state as illustrated in FIGS. 2 and 4 upon cessation of the bending movements. In the flaccid position, the tension in the tension member 32 is slight as is the frictional forces between the radiused segments 50 whereby the prosthesis is relatively flexible. In the erect/rigid state the cam member 68 is displaced longitudinally farther from the anchored end of the tension member 32 such that the tension member 32 is placed in tension and the frictional forces between the radiused segments 50 is increased whereby the prosthesis is relatively rigid.

More particularly, as illustrated in FIGS. 5 through 7, the ramp configuration 100 of the cam member 68 includes two inclined ramps 110 and 116 and four horizontal surface areas 104, 108, 114 and 120 which cooperate to define four vertical barriers 106, 112, 118, and 122 so as to define only one way travel through the ramp configuration 100. As indicated above, the cam member 68 is caused to move longitudinally away from the mounting block 84 by bending the prosthesis 20 which causes the displacement of the tension member 32, which in turn because of its fixed length, results in increased tension in the tension member 32. When the force of the tension member 32 exceeds that of the coil spring 70, the cam member 68 moves longitudinally away from the mounting block 84. Assuming the prosthesis 20 was in the flaccid state illustrated in FIGS. 1 and 3 such that the cam follower member 86 was in the positioned illustrated in FIGS. 1 and 3 at the time of bending the prosthesis 20, the cam follower end 86b would move as generally indicated by the arrow 92 from the surface 104 on the ramp configuration 100 to the surface 108. The cam follower end 86b is prevented from moving onto the surface 120 by the vertical barrier 122. The surface 108 allows for some over travel by the cam follower end 86b should the prosthesis be bent excessively. Upon cessation of the bending motion, the curvature of the prosthesis 20 will be reduced and the tension in the tension member 32 will be reduced. Accordingly, the coil spring 70 will bias the cam member 68 toward the mounting block 84 such that the cam follower end 86b will move from the surface 108 over the ramp 110 as generally indicated by the arrow 93 and onto the surface 114. The vertically extending barrier 106 will prevent the cam follower end 86b from moving back onto surface 104. The cam member 68 will continue to move toward the mounting block 84 under the influence of the coil spring 70 until the cam follower end 86b moves to the position generally indicated in FIGS. 2 and 4, whereupon it comes to rest proximate a vertical wall 130 of the cam member 68 where the force of the coil spring 70 is balanced by the force of the tension member 32. With the cam member 68 in the position shown in FIGS. 2 and 4, the prosthesis 20 is in a rigid or erect state since the tension member 32 is placed under tension by the coil spring 70 forcing the cam member toward the pivot block 84. In addition, the friction between the surfaces 56 and 54 of the radiused segments 50 is increased thereby providing the prosthesis 20 with substantial rigidity. If the prosthesis 20 is bent once again the increased tension in the tension member 32 will cause the cam member 68 to move longitudinally away from the mounting block 84. Assuming the cam follower member end 86b was in the position illustrated in FIGS. 2 and 4 at the time of bending the prosthesis 20, the cam follower end 86b will move as generally indicated by the arrow 94 from the surface 114 over the ramp 116 and onto the surface 120 since the cam follower end 86b is prevented from moving onto the ramp 110 by the vertical barrier 112. The surface 120 once again provides for some over travel by the cam follower end 86b should the prosthesis 20 be bent excessively. Upon cessation of the bending motion the prosthesis 20, the curvature of the prosthesis 20 will be reduced and the tension in the tension member 32 will corresponding be reduced. Accordingly, the cam member 68 will be biased toward the mounting block 84 by the coil spring 70 such that the cam follower end 86b will move from the surface 120 onto the surface 104 since the barrier 118 will prevent the cam follower end 86b from moving back onto the ramp surface 116. The cam member 68 will continue to move longitudinally toward the mounting block 84 until the cam follower end 86b engages vertical wall 132 of the cam member 68 whereupon the cam member 68 is retained in position and further longitudinal movement toward the mounting block 84 is prevented. With the cam member 68 in the position illustrated in FIGS. 1 and 3, the prosthesis 20 is in a flexible or flaccid state since the tension member 32 is not under tension or reduced tension and the frictional forces between the adjacent surfaces 54 and 52 of the radiused segments 50 is decreased.

As previously indicated, the entire prosthesis 20 is preferably covered with the sheath 28 of physiologically inert and pliable material to shield the prosthesis from the body tissue so as to prevent tissue interference with its function and prevent tissue damage, the sheath 28 being wedgedly secured by the clamp members 38, 40 in cooperation with the members 46, 48 near the proximal and distal ends of the prosthesis 20. The applicants have found that expanded polytetrofloralethylene (PTFE) such as the product sold by Goretex Corporation under the trademark Goretex is a suitable material. It will be appreciated that other elastomeric type, implantable material might be utilized.

Most of the internal elements are preferably made of Titanium and stainless steel. However, the radiused segments 50 and possibly and the cam member 68 are preferably made of polysulfone. It will be appreciated that other suitable materials might be utilized.

Subsequent bending and unbending may be carried out for numerous repetitions with the prosthesis 20 being alternately rigid and flaccid. The prosthesis 20 thus exhibits bistable characteristics in that it maintains either of the states until being manually changed.

It has been found that an axial elongation of two to six millimeters will generate adequate tension to maintain an erection.

In one embodiment of the present invention an axial tension member 32 is not utilized. The sheath 28 might be utilized as the primary tensioning member.

It is to be understood, however, even though numerous advantages and characteristics of the invention have been set forth in the foregoing description, together with details of the structure and function of the invention, the disclosure is illustrative only, and changes may be made in detail, especially in matters of shape, size and arrangement of parts within the principles of the present invention, to the full extent indicated by the broad general meaning of the terms in which the appended claims are expressed.

What is claimed is:

1. A penile prosthesis, comprising:
   (a) an elongated cylindrical body having a longitudinal axis and further having a distal end portion and a proximal end portion, said elongated cylindrical body including an outer elongated sheath formed from a physiologically inert and pliable material;
   (b) an articulated column of radiused segments disposed intermediate of said distal end portion and said proximal end portion, adjacent ones of said segments cooperating to form slidable joints between said adjacent ones of said segments;
   (c) an elongated tension member extending longitudinally of said elongated cylindrical body, said tension member being fixed against longitudinal movement at a first end, said articulated column being axially journaled about said tension member;
   (d) an actuator apparatus disposed intermediate of said articulated column and one of said distal and proximal end portions, said actuator apparatus including a longitudinally slideable cam member and a cam follower member pivotally mounted and fixed against longitudinal movement at a first end, said cam member being disposed intermediate of said articulated column and said cam follower member, said cam member being biased toward said cam follower member by a biasing member disposed intermediate of said articulated column and said cam member, said cam member being interconnected to a second end of said tension member, said cam member having a ramp configuration providing for one way travel along said ramp configuration by a second end of said cam follower member; and
   (e) said tension member cooperating with said cam member to displace said cam member longitudinally away from said cam follower member when the prosthesis is bent so as to place said tension member in sufficient tension to overcome said biasing member, whereby said cam member is moved longitudinally away from said cam follower member, said member moving longitudinally toward said cam follower member upon termination of the bending action so as to alternately come to rest at a first or second relative longitudinal displacement from the first end of said cam follower member, said first relative longitudinal displacement being greater than said second relative longitudinal displacement, said tension member having less tension when said cam follower member and said cam member are longitudinally displaced by said first longitudinal displacement than when said cam follower member and said cam member are longitudinally displaced by said second longitudinal displacement.

2. A penile prosthesis in accordance with claim 1, wherein at least some of said radiused segments include a bend limiting surface portion at each end, said bend limiting surface portion of adjacent radiused segments cooperating to limit the bending motion of said adjacent radiused segments.

3. A penile prosthesis in accordance with claim 1, wherein at least one of said distal and proximal end portions are removably interconnected to said elongated cylindrical body of the penile prosthesis by positive locking means.

4. A penile prosthesis in accordance with claim 3, wherein said positive locking means includes a set screw which is removably threaded into the elongated cylindrical body of the prosthesis to positively engage in a pin member molded into one of said distal and proximal end portions and inserted into an aperture in said elongated cylindrical body of the prosthesis.

5. A penile prosthesis in accordance with claim 1, wherein said distal end portion includes a reinforcing rod molded therein.

6. A penile prosthesis comprising:
   (a) a distal end;

(b) a proximal end;
(c) an outer elongated sheath formed from physiologically inert and pliable material;
(d) an articulated column of segments having slideable joints therebetween and enclosed within said sheath, said articulated column disposed intermediate of said distal and proximate ends;
(e) an actuator apparatus disposed intermediate of said articulated column and one of said distal and proximal end portions, said actuator apparatus including a cam member and a cam follower member;
(f) biasing means cooperating with said actuator apparatus to longitudinally bias said cam member and said cam follower member toward one another; and
(g) tension means cooperating with said actuator apparatus to longitudinally bias said cam member and said cam follower member away from one another when said tension means is placed in tension, said tension means causing said cam member and said cam follower member to longitudinally move apart when placed in sufficient tension to overcome said biasing means, said tension means being placed in said sufficient tension by applying a bending force on the prosthesis to cause bending of the same, said cam member and said cam follower member moving longitudinally toward one another upon removal of said bending force, said cam follower member and said cam member comming to rest a first or second relative longitudinal displacement between one another upon removal of said bending force, said cam member and said cam follower member being farther apart in said first relative longitudinal displacement, said actuator apparatus cooperating with said tension means to compress said articulated column when in said second relative longitudinal displacement and further cooperating with said tension means to place said articulated column in a noncompressed state when in said first relative longitudinal displacement.

7. A bistable penile prosthesis having an erect state and a flaccid state, comprising:
(a) an elongated cylindrical body having a longitudinal axis and a distal end portion and a proximal end portion, said elongated cylindrical body being bendable into a first curved configuration;
(b) an articulated column of radiused segments disposed intermediate of said distal end portion and said proximal end portion, adjacent ones of said segments cooperating to form slideably joints between said adjacent ones of said segments;
(c) an outer elongated sheath formed from physiologically inert and pliable material enclosing said articulated column;
(d) actuator means disposed intermediate of said articulated column and one of said distal and proximal end portions, said actuator means including cam means and cam follower means, said cam means providing a pathway for only one-way travel therealong by said cam follower means;
(e) biasing means cooperating with said actuator means to longitudinally bias said cam means and said cam follower means toward one another;
(f) tension means cooperating with said actuator means to longitudinally bias said cam means and said cam follower means away from one another when said tension means is placed in tension, said tension means causing said cam means and said cam follower means to move longitudinally away from one another when said elongated cylindrical body of the prosthesis is bent into said first curved configuration, said biasing means longitudinally moving said cam means and said cam follower means toward one another when said elongated cylindrical body of the prosthesis is returned to a second configuration having less curvature than said first configuration; and
(g) said cam means and said cam follower means alternately returning to a first or second relative longitudinal displacement between one another upon return of said elongated cylindrical body of the prosthesis to said second configuration, said cam means and said cam follower means being further apart when displaced by said first relative longitudinal displacement, said cam follower means cooperating with said cam means to maintain said second relative longitudinal displacement, said biasing means and said tension means counterbalancing one another when said cam means and said cam follower means are in said first relative longitudinal displacement, the prosthesis being in the erect state when said cam means and said cam follower means are in said second relative longitudinal displacement and in the flaccid state when said cam means and said cam follower means are in said first relative longitudinal displacement.

* * * * *

UNITED STATES PATENT AND TRADEMARK OFFICE
CERTIFICATE OF CORRECTION

PATENT NO. : 4,541,420
DATED : September 17, 1985
INVENTOR(S) : Richard A. Helms et al.

It is certified that error appears in the above-identified patent and that said Letters Patent is hereby corrected as shown below:

Col. 2, line 67, delete "flacid" and insert --flaccid--.

Col. 3, line 20, delete "aparatus" and insert --apparatus--.

Col. 3, line 37, delete "axially" and insert --axial--.

Col. 3, line 60, delete "cavenosal" and insert --cavernosal--.

Col. 4, line 51, delete "acutator" and insert --actuator--.

Col. 5, line 32, delete "bullet-or" and insert --bullet- or--.

Col. 5, line 56, delete "claim" and insert --clamp--.

Col. 5, lines 57-58, delete "aperatures" and insert --apertures--.

Col. 5, line 62, delete "sili cone" and insert --silicone--.

Col. 6, line 40, delete "segements" and insert --segments--.

Col. 11, line 30, delete "comming" and insert --coming--.

Signed and Sealed this

Eighteenth Day of November, 1986

Attest:

DONALD J. QUIGG

Attesting Officer     Commissioner of Patents and Trademarks